United States Patent
Hasegawa

(10) Patent No.: US 12,201,434 B2
(45) Date of Patent: Jan. 21, 2025

(54) INTENTION DECODING APPARATUS AND INTENTION CONVEYANCE ASSIST APPARATUS

(71) Applicant: NATIONAL INSTITUTE OF ADVANCED INDUSTRIAL SCIENCE AND TECHNOLOGY, Tokyo (JP)

(72) Inventor: Ryohei Hasegawa, Ibaraki (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 1373 days.

(21) Appl. No.: 16/094,637

(22) PCT Filed: Apr. 6, 2017

(86) PCT No.: PCT/JP2017/014383
§ 371 (c)(1),
(2) Date: Sep. 30, 2019

(87) PCT Pub. No.: WO2017/179486
PCT Pub. Date: Oct. 19, 2017

(65) Prior Publication Data
US 2020/0037911 A1  Feb. 6, 2020

(30) Foreign Application Priority Data
Apr. 14, 2016 (JP) ................ 2016-081229

(51) Int. Cl.
*A61B 5/377* (2021.01)
*A61B 8/08* (2006.01)
(Continued)

(52) U.S. Cl.
CPC ............ *A61B 5/377* (2021.01); *A61B 8/0808* (2013.01); *G06F 3/01* (2013.01); *G09B 21/00* (2013.01); *G16H 10/40* (2018.01); *G16H 50/70* (2018.01)

(58) Field of Classification Search
CPC ..... A61B 5/377; A61B 8/0808; A61B 5/4064; A61B 5/372; A61B 5/16; G06F 3/01; G09B 21/00; G16H 10/40; G16H 50/70
See application file for complete search history.

(56) References Cited

U.S. PATENT DOCUMENTS 5,083,571 A * 1/1992 Prichep ............... A61B 5/16
600/544
2004/0243328 A1* 12/2004 Rapp .................. A61B 5/4094
702/71
(Continued)

FOREIGN PATENT DOCUMENTS

JP  2004275619 A  10/2004
JP  2005021569 A   1/2005
(Continued)

OTHER PUBLICATIONS

Donchin, Emanuel et al., The Mental Prosthesis: Assessing the Speed of a P300-Based Brain-Computer Interface, IEEE Transactions on Rehabilitation Engineering, 2000.06, vol. 8 No. 2, pp. 174-179.
(Continued)

*Primary Examiner* — Devin B Henson
*Assistant Examiner* — Evelyn Grace Park
(74) *Attorney, Agent, or Firm* — CANTOR COLBURN LLP

(57) ABSTRACT

An intention decoding apparatus and a decoding method that quickly and precisely analyze brain waves for decoding an intention decision without requiring an advance brain wave measurement for, for example, a calibration step, and an intention conveyance assist apparatus, an intention conveyance assist system, and a program using a decoding result of the intention decision in the brain. The intention decoding apparatus that analyzes brain waves to decode an intention performs a process to examine a dispersion by classifying brain wave data of event-related potentials corresponding to a plurality of stimulus events into any one stimulus event and the other stimulus events among the plurality of stimulus events, on all the stimulus events, and identifies a classification where the dispersion becomes maximum to identify the one stimulus event in the classification as the intention. The intention conveyance assist apparatus includes a presentation unit that presents a decoding result.

5 Claims, 4 Drawing Sheets

(51) Int. Cl.
*G06F 3/01* (2006.01)
*G09B 21/00* (2006.01)
*G16H 10/40* (2018.01)
*G16H 50/70* (2018.01)

(56) References Cited

U.S. PATENT DOCUMENTS

| | | | |
|---|---|---|---|
| 2010/0145215 A1* | 6/2010 | Pradeep | A61B 5/377 |
| | | | 600/546 |
| 2012/0069247 A1 | 3/2012 | Morikawa et al. | |
| 2013/0158883 A1 | 6/2013 | Hasegawa et al. | |
| 2015/0026195 A1 | 1/2015 | Hasegawa | |
| 2017/0007147 A1 | 1/2017 | Hasegawa | |

FOREIGN PATENT DOCUMENTS

| | | |
|---|---|---|
| JP | 2010274035 A | 12/2010 |
| JP | 2012053656 A | 3/2012 |
| JP | 2012073329 A | 4/2012 |
| JP | 2013178601 A | 9/2013 |
| WO | 2015111331 A1 | 7/2015 |

OTHER PUBLICATIONS

Hasegawa et al., "Single trial-based prediction of a go/no-go decision in monkey superior colliculus", Neural Networks 19 (2006) 1223-1232.

International Search Report; International Application No. PCT/JP2017/014383; Date of Completion of Search Jun. 7, 2017; Date of Mailing Jun. 20, 2017; 2 pages.

Ryohei Hasegawa, "EEG-based Brain-Machine Interfaces for Practical Communication Aid", The Journal of the Institute of Electronics, Information and Communication Engineers, Sep. 1, 2012 (Sep. 1, 2012), vol. 95, No. 9, pp. 834-839.

Written Opinion of the International Searching Authority; International Application No. PCT/JP2017/014383; International Filing Date Apr. 6, 2017; Date of Mailing Jun. 20, 2017; 4 pages.

* cited by examiner

INTENTION DECODING APPARATUS AND INTENTION CONVEYANCE ASSIST APPARATUS

CROSS REFERENCE TO RELATED APPLICATIONS

This is a U.S. national stage of application No. PCT/JP2017/014383, filed on 6 Apr. 2017. Priority under 35 U.S.C. § 119 (a) and 35 U.S.C. § 365 (b) is claimed from Japanese Patent Application No. 2016-081229, filed 14 Apr. 2016, the disclosure of which is also incorporated herein by reference.

BACKGROUND OF THE INVENTION

The present invention relates to a decoding apparatus and an intention decoding method that analyze brain waves for decoding an intention decision, and an intention conveyance assist apparatus, an intention conveyance assist system, and a program using a decoding result of this intention decision.

There have been various studies on the relationship between human thought or behavior and brain activity, in recent years. Attention is being focused on Brain-Machine Interface (BMI) technology for controlling external equipment or conveying one's intention to another person by noting a biosignal of, e.g., brain activity.

A virtual decision function, and a calculation method therefor have previously been proposed. For example, JP 2012-053656 A describes a method for predicting an alternative behavior from a neural activity such as a single neural activity of a monkey.

An intention conveyance assist apparatus and a method for ensuring conveyance of an intention by brain activity analysis have also been proposed as described in JP 2012-053656 A and JP 2012-073329 A. The technologies described in JP 2012-053656 A and JP 2012-073329 A ensure, for example, an assist of the conveyance of an intention of a person with motor impairment having difficulty speaking or writing, and of a person with severe motor impairment having difficulty performing an input operation on various devices using hands, legs, or similar organs.

A technique for showing a map of information representations in the brain by brain wave analysis performed on general test subjects, including non-handicapped persons as described in JP 2010-274035 A. An apparatus and a method for ranking the objects to be investigated by brain wave analysis as described in JP 2013-178601 A. An apparatus and a method for evaluating a cognitive function of a test subject by brain wave analysis is described in WO 2015/111331.

BRIEF SUMMARY OF THE INVENTION

The impairment of motor function, which is the main symptom of the stroke or the intractable neurological diseases, makes not only an activity of daily living but also an intention conveyance to the family and a caregiver difficult. Therefore, the conventional assist technique focusing on the remaining motor function is often not effective for a person with severe motor impairment whose symptom affects the entire body.

It has been desired to ensure decoding an intention decision in the brain at high speed and with high accuracy by analyzing brain wave data. The inventor has proposed an intention conveyance apparatus technique (also referred to as "Neuro Communicator") based on the brain wave especially measured on the scalp, as a BMI technology that directly couples the brain to the machine, for communication assist for the person with severe motor impairment (see, for examples, JP 2012-053656 A, JP 2012-073329 A, and JP 2010-274035 A). The Neuro Communicator is a system that allows selection of one (target) from a plurality of pictograms displayed on a screen of a personal computer to express a related message, by decoding the intention in the brain focusing on an event-related potential that reflects a selective attention of a user. The proposition up to the present has shown that use of a compact wireless electroencephalograph or a resin headgear ensures a facilitated measurement of high-quality brain wave data, and that a proposed algorithm ensures decoding of the target from the brain wave at high speed and with high accuracy.

On the premise of the use of the above-described Neuro Communicator, in order to decode a brain wave pattern (time-series data of the event-related potential that is different depending on whether it is the target or a non-target) unique to each user by a pattern recognition technique such as a linear discriminant analysis, a process of data collection (hereinafter also referred to as "calibration") to optimize values of prediction-model-type weighting coefficients has been indispensable.

FIG. 6 is an explanatory drawing of a procedure of conventional brain wave decoding that requires an instruction signal. As illustrated in FIG. 6, the brain wave decoding is performed in the following steps (1), (2), and (3). FIG. 6 is an explanatory drawing taking a case where there are eight stimulus events as an example.

(1) Step of Obtaining Data with Instruction Signal

One of a plurality of stimulus events as "target" has been instructed to a test subject. Then, the plurality of stimulus events are presented, and the brain wave is measured as a reaction of the brain of the test subject with respect to the stimulus events. As in (1) in the drawing, with respect to stimulus events ID1 to ID8, brain wave data that the test subject has reacted taking ID1 as "target" and the others as "non-targets," brain wave data that the test subject has reacted taking ID2 as "target" and the others as "non-targets," and subsequently similar brain wave data are obtained. The obtained brain wave data includes the brain wave data when the test subject has selected the instructed target as the target, and the brain wave data shown by the test subject with respect to other than the instructed target. The instruction is given to all the stimulus events as "targets" to obtain the brain wave data. This brain wave data is used as the brain wave data with the instruction signal.

(2) Step of Creating One Type of Model Expression

From the brain wave data with the instruction signal obtained in (1), a discriminant model expression (also referred to as "discriminant function") as illustrated in (2) in the drawing is created. The brain wave data are different, by the stimulus event, between the brain wave data in the case of the target and the brain wave data in the case of the non-target, depending on channels by electrode positions and elapsed times after the stimulus. Based on the respective channels and the elapsed times after the stimulus, the weighting coefficients in the discriminant analysis can be obtained. In the drawing, the discriminant model expression is a discriminant function that divides the brain wave data into a first class (target) when a discrimination score is positive and a second class (non-target) when the discrimination score is negative. The term y is the discrimination score.

(3) Step of Decoding New Data Without the Instruction Signal

A plurality of stimulus events are presented to the test subject without instructing the target, thus measuring the brain wave of the test subject. For the obtained brain wave data without the instruction signal, using the discriminant model expression obtained in (2), the discrimination score for each stimulus event is calculated. A stimulus event indicating the maximum discrimination score among the calculated discrimination scores is decided as the stimulus event for which the intention decision has been made in the brain. To more enhance the accuracy of the decoding, the discrimination is performed with a discrimination score accumulated with respect to an identical stimulus event, as the discrimination score.

The above-described steps (1) and (2) constitute a calibration step. The calibration step presents "a condition to set any pictogram designated on a system side as the target and the other pictograms as the non-targets" to the user, and obtains the event-related potential with respect to each pictogram in this condition. That is, one type of discriminant model expression is generated in a condition where there is "instruction signal" indicating whether each brain wave data is for the target or for the non-target. There is a case where the target pictogram may be changed in the middle of the calibration for tagging independent of the pictogram, with the instruction from the system. Also in this case, a content (whether it is the target) of the instruction signal is decided corresponding to a definition on the system side.

A concrete example of the calibration will be described. The calibration step uses a plurality of pictograms (for example, eight types of pictograms) displayed on the screen, similar to those in an intention decoding implementation step after the calibration, as stimulus objects. The conventional method instructs a specific pictogram as "target" to the test subject, and then, sequentially presents the pictograms. The pictograms are pseudorandomly presented for every type. A unit to pseudorandomly present the pictograms once for every type is referred to as "block." The block is repeated multiple times. A repetition to present the stimulus with respect to an identical target is referred to as "one game." Usually, after the start of each game, the user performs a work to count the number of presentations of the target in his/her head. This is for calling an attention of the user to the target. However, insofar as the attention of the user to the pictogram is kept from a perspective of whether the pictogram is the target, the count is not necessarily required. The brain wave data discriminated where it is the brain wave data immediately after presenting the instructed target or the brain wave data immediately after presenting the other non-target is referred to as "brain wave data with the instruction signal." When the brain wave data with the instruction signal is used for creating the discriminant model expression, several games are performed for the calibration. In each game, an experimenter (system side) defines one type of, for example, eight types of pictograms as the target, and teaches the test subject (user side) about it. In view of this, the other seven types automatically become the non-targets. The stimulus presentations for the several games optimize the weighting coefficients in the discriminant model expression, after obtaining sufficient data in a relationship with the number of items of the discriminant model expression (the number of necessary data increases in proportion to the number of the items). Usually, the setting is performed such that an output of the discriminant model expression becomes a positive value with respect to the target and a negative value with respect to the non-target.

The use of the discriminant model expression generated by this sequence of works allows decoding with respect to subsequent new data (without the instruction signal).

Preliminarily performing the calibration ensures estimation which pictogram has been the target, also with respect to a set (without the instruction signal) of the brain wave data when the user conveniently has selected the target, in the intention decoding implementation step after the calibration.

However, such calibration for model generation is an extra process for a severe patient to exhaust himself/herself. The inventor has been examining a possibility of a method that can omit this process.

As described above, the conventional intention decoding technique by brain wave analysis has required brain wave measurement for creating the discriminant analysis function (discriminant model expression), and has required the step (calibration step) of creating the discriminant model based on the brain wave data obtained with this measurement. Thus, there is a problem to take a time for obtaining the brain wave data and for a discriminant model creation process based on it. Meanwhile, there is a problem that the discriminant model expression cannot be created without preparing the brain wave data for the calibration. Additionally, there is a problem that an accurate intention decision in the brain cannot be decoded without premising the calibration step.

The present invention aims to overcome the above problems and an object of the present invention is to provide a decoding apparatus, a decoding method, a decoding system, and a program that quickly and precisely analyze brain waves for decoding an intention decision without requiring an advance preparation step, and an intention conveyance assist apparatus, an intention conveyance assist method, an intention conveyance assist system, and a program using a decoding result of the intention decision in the brain.

In order to achieve the objects, the present invention has the following features:

(1) The present invention is an intention decoding apparatus that analyzes brain waves to decode an intention. The intention decoding apparatus performs a process to examine a dispersion by classifying brain wave data of event-related potentials corresponding to a plurality of stimulus events into any one stimulus event and the other stimulus events among the plurality of stimulus events, on all the stimulus events, and identifies a classification where the dispersion becomes maximum to identify the one stimulus event in the classification as the intention.

(2) In the (1), the process is a process to obtain a discriminant model expression of a discriminant function that discriminates one stimulus event and the other stimulus events among the plurality of stimulus events to calculate a discrimination score of the one stimulus event. The intention decoding apparatus identifies the classification of the stimulus event where the dispersion becomes maximum based on values of the obtained discrimination scores.

(3) The present invention is an intention conveyance assist apparatus including a presentation unit that presents a decoding result of the intention decoding apparatus according to the (1) or (2).

(4) The present invention is an intention conveyance assist system including a stimulus event presentation apparatus that presents stimulus events, an electroencephalograph, a processing apparatus that processes brain wave data from the electroencephalograph, and a presentation apparatus of a process result. The stimulus event presentation apparatus presents each of a plurality of stimulus events one or more times. The electroencephalograph measures a brain wave immediately after the presentation of the stimulus event by the stimulus event presentation apparatus. The processing apparatus performs a process to examine a dispersion by classifying brain wave data of event-related potentials corresponding to a plurality of stimulus events into any one stimulus event and the other stimulus events among the plurality of stimulus events, on all the stimulus events, and identifies a classification where the dispersion becomes maximum to identify the one stimulus event in the classification as the intention. The presentation apparatus presents the process result.

(5) The present invention is an intention decoding method of analyzing brain waves to decode an intention. The intention decoding method performs a process to examine a dispersion by classifying brain wave data of event-related potentials corresponding to a plurality of stimulus events into any one stimulus event and the other stimulus events among the plurality of stimulus events, on all the stimulus events, and identifies a classification where the dispersion becomes maximum to identify the one stimulus event in the classification as the intention.

(6) The present invention is a program. The program is a program for causing a computer to function as stimulus event presentation means that presents each of a plurality of stimulus events one or more times, process means that performs a process to examine a dispersion by classifying brain wave data of event-related potentials corresponding to a plurality of stimulus events into any one stimulus event and the other stimulus events among the plurality of stimulus events, on all the stimulus events, and identifies a classification where the dispersion becomes maximum to identify the one stimulus event in the classification as the intention, and presentation means that presents the identified one stimulus event.

The present invention allows the analysis of the brain wave without requiring the advance preparation for decoding the intention decision in the brain. With the present invention, a content for which the intention decision is made in the brain can be decoded quickly with high accuracy. The presentation of the decoding result by the intention decision decoding of the present invention in various means allows the intention conveyance to the third person such as a helper.

The present invention is effective for not only a non-handicapped person but also a person with motor impairment and the like.

DETAILED DESCRIPTION

Figure 1:
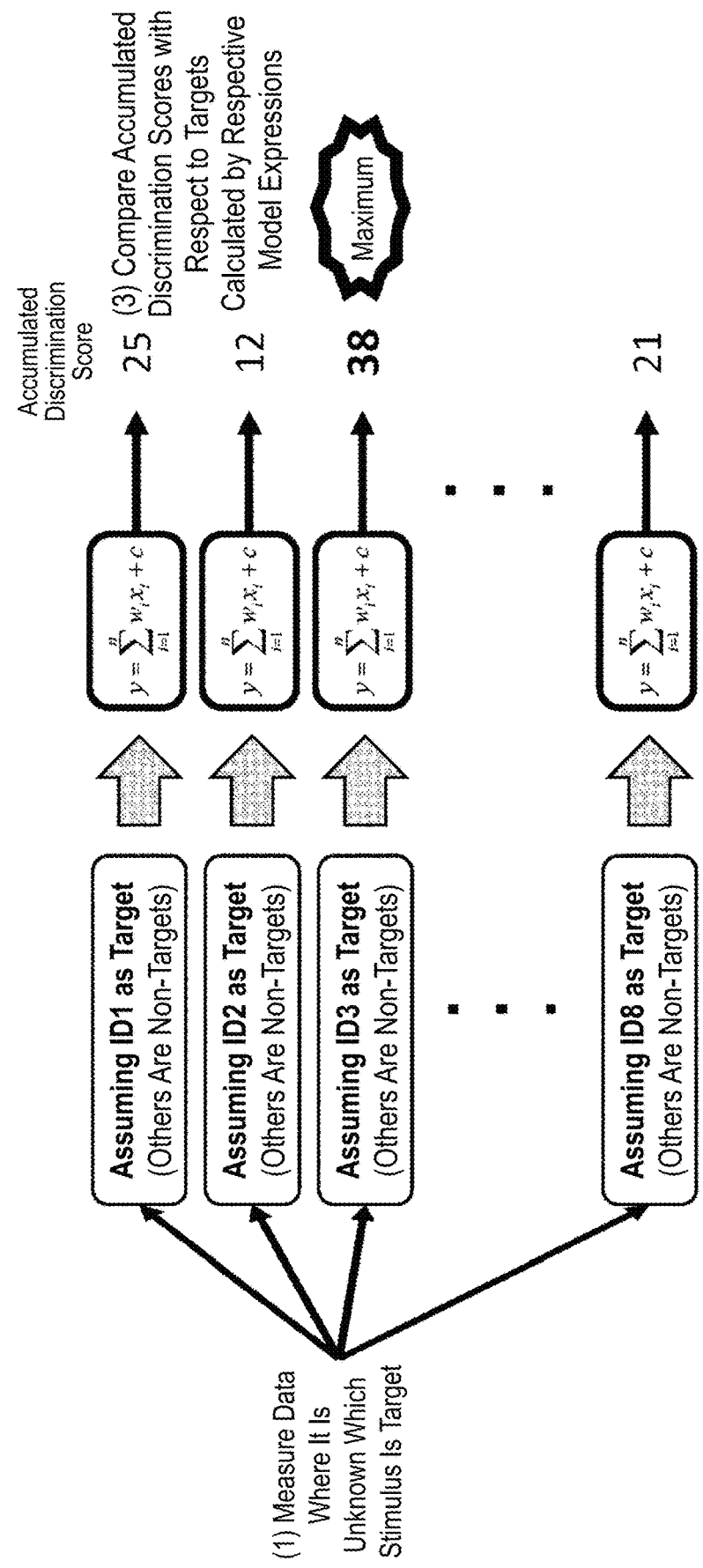
FIG. 1 is an explanatory drawing of a brain wave decoding procedure that does not require an instruction signal according to an embodiment of the present invention.

Embodiments of the present invention will be described in the following.

The present invention performs brain wave decoding that does not require any instruction signal. A description will be given of a principle of the brain wave decoding in a condition where there is no instruction signal of the present invention. The principle that ensures decoding which stimulus is a target though a calibration is not performed is based on a hypothesis that "since a class of brain wave data related to a target stimulus is significantly different from remaining all the classes of brain wave data related to non-target stimuli in their features, a dispersion of a feature quantity examined by performing a classification with this combination should be larger than a dispersion of a feature quantity examined by performing a classification with any other combination." Based on this hypothesis, in the case where a stimulus assumed as the target was actually the target, a discrimination score with respect to the measured brain wave data should tend to be high compared with other cases. Other than the highness of the discrimination score provided to the target, it is also possible to perform a decoding focusing on a lowness of an average value of the discrimination scores of the remaining stimuli as the non-targets, or a decoding focusing on both of the highness of the discrimination score of the target and the lowness of the average value of the discrimination scores of the non-targets. In a multivariate analysis used in this application, the brain wave data has been analyzed, and in order to examine a dispersion of a feature quantity of this brain wave data, for example, a discriminant analysis has been performed on the brain wave data to examine a dispersion of the discrimination scores.

In the present invention, it is determined which stimulus among a plurality of stimuli is "stimulus as a decision object when an intention decision is made in the brain," from the brain wave data with respect to the plurality of stimuli. Therefore, the brain wave data is distinguished into two groups: "stimulus as the decision object when the intention decision is made in the brain" (for example, the discrimination score is large) and "stimulus other than the stimulus as the decision object when the intention decision is made in the brain" (for example, the discrimination score is small), with the discrimination score by the discriminant analysis. Here, in the present invention, for example, a discriminant model expression is not preliminarily created, and the discriminant model expression for discriminating all of a plurality of stimulus events from other stimulus events when the stimulus event is assumed as the stimulus event for which the intention decision is made in the brain is created. Then, a stimulus event indicating the maximum discrimination score among the discrimination scores calculated by this discriminant model expression is decided as the stimulus event for which the intention decision is made in the brain.

FIG. 1 is a schematic drawing describing brain wave decoding to decode the intention decision in the brain of the present invention. In the embodiment of the present invention, as illustrated in FIG. 1, in the following steps (1), (2), (3), and (4), the intention decision in the brain with the brain wave is decoded.

FIG. 1 illustrates an example where there are eight stimulus events.

(1) Step of measuring data where it is unknown which stimulus is the target. A plurality of stimulus events are presented to a test subject without instructing the target, and then, the brain waves of the test subject with respect to the presentation of the stimulus events are measured.

(2) Step of generating a plurality of discriminant model expressions by assuming the respective stimuli as the targets. The discriminant model expression is created as illustrated in (2) in the drawing from the brain wave data without the instruction signal obtained in (1). A creation method is identical to the conventional one. However, in this embodiment, there is no instruction signal. Thus, a plurality of model expressions are generated by assuming the respective stimuli as the targets as follows. A discriminant model expression (assuming ID1 as the target) is created using the brain wave data without the instruction signal, assuming ID1 as the target, and the others as the non-targets. A discriminant model expression (assuming ID2 as the target) is created using the brain wave data without the instruction signal, assuming ID2 as the target, and the others as the non-targets. Similarly, as a discriminant model expression (assuming ID3 as the target), . . . , and a discriminant model expression (assuming ID8 as the target), eight types of discriminant model expressions are created. Here, the drawing simply illustrates that expressions of a discrimination score y are identical. However, weighting coefficients $w_i$ and constant terms c with respect to the respective brain wave data are different in the respective discriminant expressions. In the expression of y, x is the value of brain wave data (voltage) at a certain point in time of a certain channel. As to the type of x, there are as many types (n) as the product of the number of channels (which corresponds to the number of measurement locations because the brain wave data are obtained at a plurality of measurement locations on the scalp of the head of the test subject) and data points (respective time windows after the respective stimuli).

(3) Step of comparing the accumulated discrimination scores with respect to the target, which are calculated by the respective model expressions The discrimination score for each stimulus event is calculated for the brain wave data without the instruction signal obtained in (1), using the discriminant model expression (assuming ID1 as the target) obtained in (2). A stimulus event indicating the maximum discrimination score (hereinafter referred to as "maximum discrimination score (discriminant model expression (assuming ID1 as the target))") among the calculated discrimination scores is obviously ID1 assumed as the target. Similarly, the discrimination score for each stimulus event is calculated for the brain wave data without the instruction signal obtained in (1), using the discriminant model expression (assuming ID2 as the target) obtained in (2). A stimulus event indicating the maximum discrimination score (hereinafter referred to as "maximum discrimination score (discriminant model expression (assuming ID2 as the target))") among the calculated discrimination scores is obviously ID2 assumed as the target. In the following, similarly, the maximum discrimination scores (discriminant model expressions (assuming ID3 to ID8 as the targets)) are obtained using the respective discriminant model expressions (assuming ID3 to ID8 as the targets). To more enhance an accuracy of the decoding, the decoding is performed with a discrimination score accumulated with respect to an identical stimulus event, as the discrimination score. The obtained maximum discrimination scores (discriminant model expressions (assuming ID1 to ID8 as the targets)) are illustrated as 25, 12, 38, . . . 21, as the accumulated discrimination scores in the drawing. The accumulated discrimination scores are compared.

The steps in (2) and (3) are steps that perform a process to examine a dispersion of the feature quantity by classifying the brain wave data of the event-related potentials corresponding to the plurality of stimulus events into any one stimulus event and the other stimulus events among the plurality of stimulus events, on all the stimulus events.

(4) Step of identifying which is the stimulus event to which the discriminant model expression whose discrimination score is maximum is provided It is to identify which of ID1 to ID8 is the stimulus event to which the discriminant model expression whose discrimination score is maximum is provided, among the maximum discrimination scores (discriminant model expressions (assuming ID1 to ID8 as the targets)) obtained in (3). In the example in FIG. 1, the stimulus event ID3 whose accumulated discrimination score is 38 is identified to be a decoding result. The decoding result (stimulus event ID3) is presented as a content for which the intention decision is made in the brain.

The step in (4) is a step of identifying the classification of the stimulus event where the dispersion of the feature quantity becomes maximum to identify the stimulus event in this classification as the intention.

According to the present invention, focusing on a brain activity, particularly an event-related potential indicating the type of the brain wave recorded on the scalp, the reaction of the brain to the presentation of a stimulus event is analyzed. Specifically, the embodiment of the present invention includes the elements of stimulus event presentation, brain wave measurement, brain wave data analysis, and presentation of an analysis result. The stimulus event includes a visual stimulus displayed on a screen, an audio stimulus presented with sound, a tactile stimulus with, for example, vibration to the skin, and another taste or olfactory stimulus.

Figure 2:
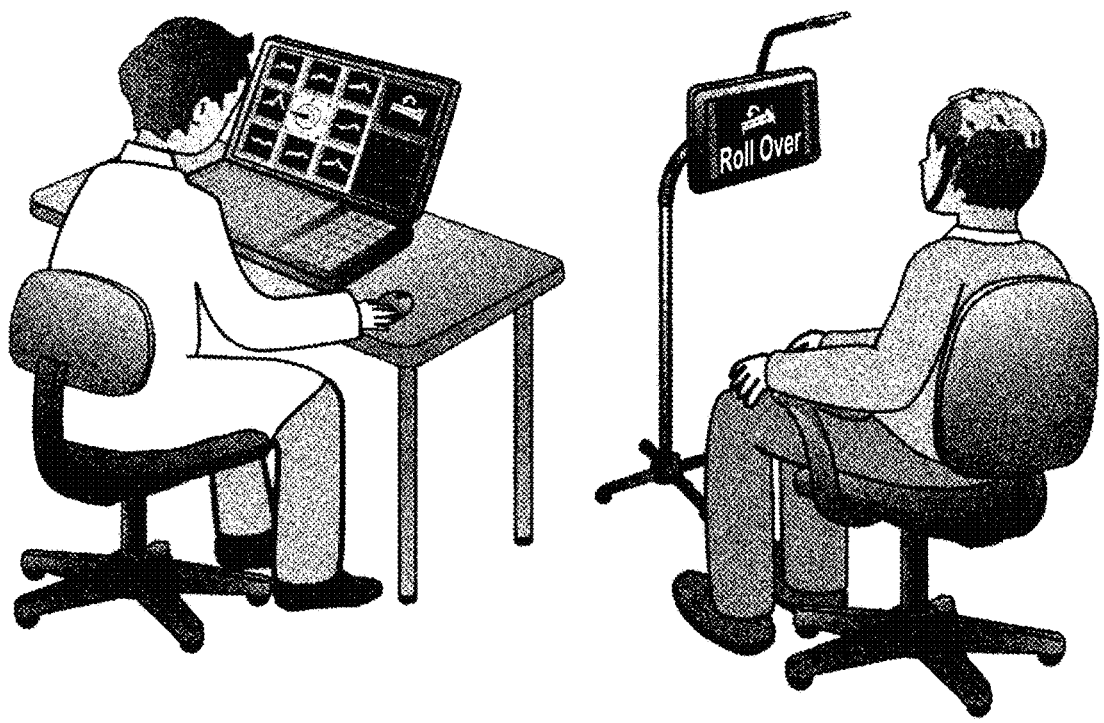
FIG. 2 is an explanatory drawing of a brain wave decoding apparatus according to the embodiment of the present invention.

FIG. 2 is an explanatory drawing of a brain wave decoding apparatus in the embodiment of the present invention. The apparatus used in the embodiment of the present invention includes a sub-monitor for test subject (hereinafter also referred to as "user"), a headgear for brain wave measurement worn by the test subject, and a processing apparatus (for example, a computer) for stimulus presentation control and data analysis. The stimulus event for the test subject is presented on a display screen of the sub-monitor for test subject. The processing apparatus (for example, a computer) for stimulus presentation control and data analysis, the sub-monitor for test subject, and the display screen or, for example, an audio-output device that presents the decoding result can be achieved by one computer.

The present embodiment will be described with reference to FIGS. 1 to 5. The decoding is performed using the brain wave decoding apparatus as in FIG. 2.

Figure 3:
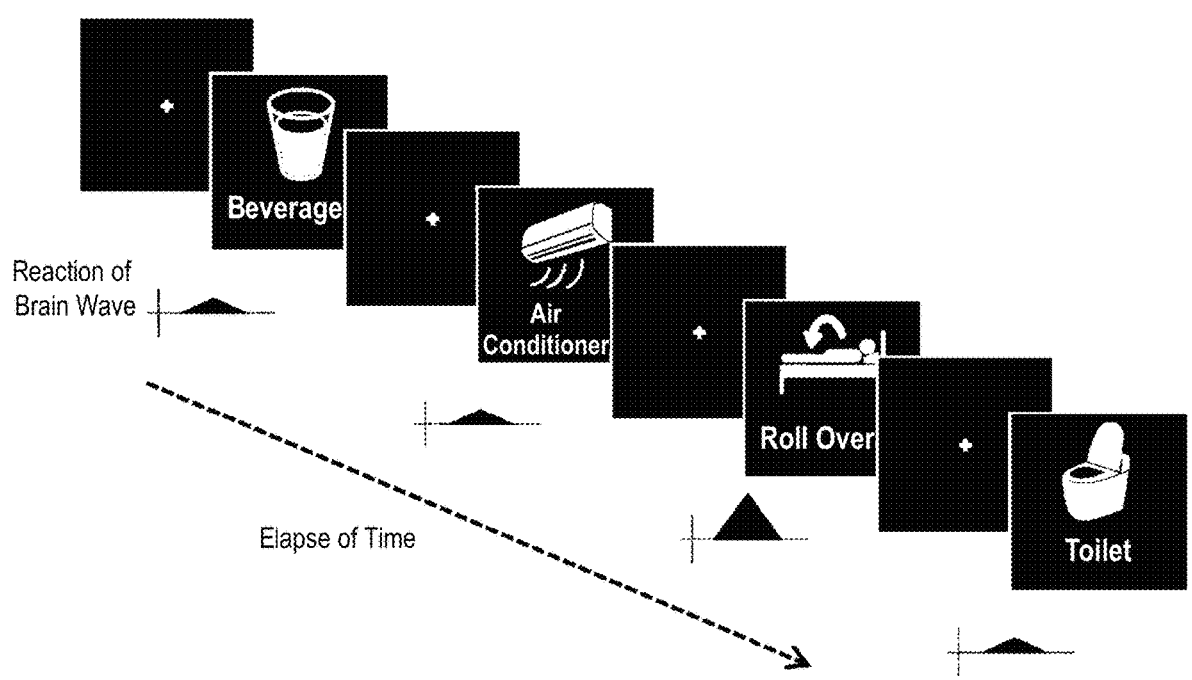
FIG. 3 is a drawing that illustrates stimulus presentations of a cognitive task in a brain wave decoding method according to the embodiment of the present invention with the time course, and describes a difference in reaction of the brain wave with respect to the respective stimulus presentations.

FIG. 3 is a drawing schematically illustrating a plurality of stimulus event presentations as cognitive tasks for decoding the intention decision in the brain and brain wave reactions in the user with respect to them according to the present embodiment, together with the time course. As illustrated in FIG. 3, stimulus events (also referred to as attention invoking events or test stimulus events), such as simple pictures, are presented to the user one event (one sheet) at a time. Then, the brain wave of the user having seen the events is measured, and this brain wave is analyzed by a brain wave analysis/processing apparatus, such as a computer. The stimulus events may include, for example, signs, illustrations, drawings, and photographs. This differs according to a content that the user wants to use as the presentation of the intention decision in the brain. For example, as in FIG. 3, the display screen of pictograms representing assistance contents desired by the user, such as "(want to drink) Beverage," "(want to turn on) Air Conditioner," "(want to) roll over," and "(want to go to) Toilet."

The detail of the cognitive tasks, in which the brain wave decoding is ensured in a state without the instruction signal, will be described.

For example, a display screen of eight types of pictograms is used as the stimulus event. After the cognitive task is started, the pictograms are sequentially presented. The time per presentation of each pictogram is 250 milliseconds, and the next pictogram is presented after a blank of 375 milliseconds. A unit of pseudorandomly presenting the pictograms once for every type is referred to as "block." The block is repeated multiple times. A repetition of the stimulus presentation with respect to an identical target (an event set in the brain by the user, an event for which the intention decision has been made in the brain by the user) is referred to as "one game."

After the start of the game, the user performs a work to count the number of presentations of the target in his/her head. The counting work is for calling an attention of the user to the target. However, insofar as the attention of the user to the pictogram is kept from a perspective of whether the pictogram is the target, the count is not necessarily required. Other than the method to present the pictograms one by one, there is a case where, while continuing to present all the pictograms on the screen, attention-getting is performed on the pictograms one by one using any cue stimulus. For example, a luminance of the pictogram is instantaneously changed, or words and illustrations are superimposed on the pictogram and presented.

In this embodiment, as described above, the user, while performing the cognitive task, counts the number of presentations of the target in his/her head. However, the setting of the target and the non-target is performed only in his/her own brain, and it is absolutely not necessary to let an experimenter (system side) know which stimulus is the target. Nonetheless, the decoding of new data is ensured without performing the calibration.

The brain wave data obtained by the measurement is analyzed by the steps of the steps (2), (3), and (4) in FIG. 1.

Figure 4:
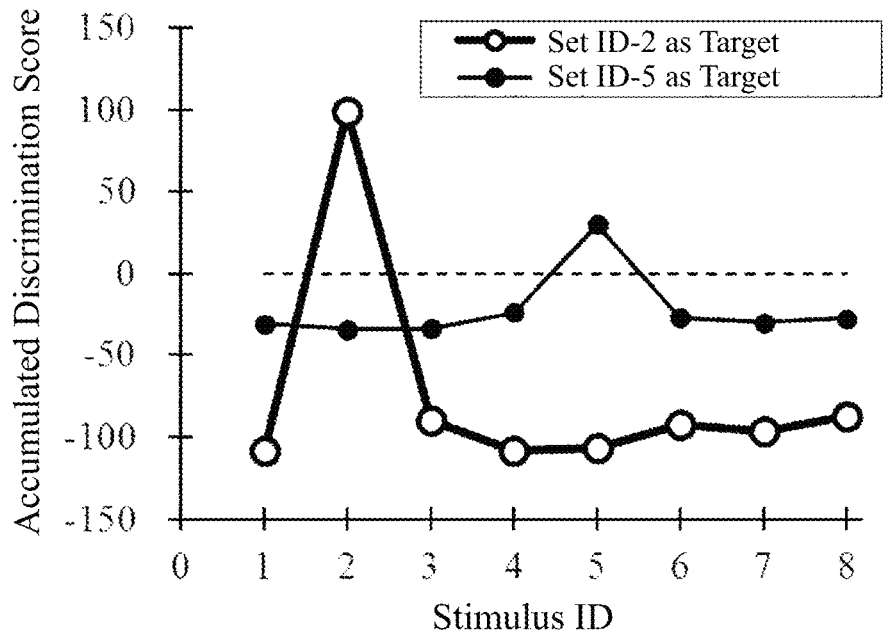
FIG. 4 is an explanatory drawing of an example to obtain an accumulated discrimination score with respect to all the stimuli when a stimulus assumed as a target is ID2 or ID5 with respect to the brain wave data in the embodiment of the present invention.

The following describes that the decoding of the target is ensured without performing the calibration, using practical experimental data. FIG. 4 is a drawing illustrating a comparison of the accumulated discrimination scores with respect to all the stimuli, when the stimulus assumed as the target is changed. For example, in FIG. 4, the discrimination scores of the respective IDs were calculated using the discriminant model expression when the classification was performed such that the stimulus of ID5 was assumed as the target and the other stimuli were assumed as the non-targets. In the experiment, the discrimination scores were compared as the plurality of accumulated data. A thin polygonal line connecting black circles is made by plotting the discrimination scores of the respective IDs calculated by the discriminant model expression created assuming ID5 as the target. Consequently, as is obvious, the discrimination score with respect to the stimulus of ID5 is higher than the discrimination scores of any other stimuli. On the other hand, when a similar analysis is performed assuming ID2 as the target, the discrimination score of ID2 is much higher than the discrimination scores of any other stimuli. A bold polygonal line connecting white circles is made by plotting the discrimination scores of the respective IDs calculated by the discriminant model expression created assuming ID2 as the target. Furthermore, it is found that a value of "maximum discrimination score (discriminant model expression (assuming ID2 as the target))" calculated by the discriminant model expression (assuming ID2 as the target) is higher than a value of "maximum discrimination score (discriminant model expression (assuming ID5 as the target))" calculated by the discriminant model expression (assuming ID5 as the target).

Figure 5:
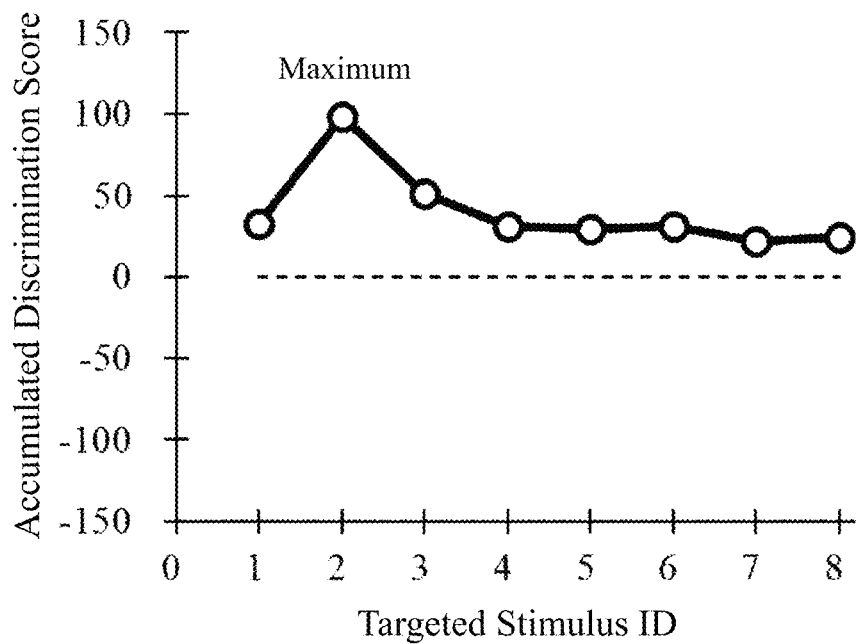
FIG. 5 is an explanatory drawing of an example to obtain the accumulated discrimination score of the target stimulus when the stimuli assumed as targets are ID1 to ID8 with respect to the brain wave data in the embodiment of the present invention.
Figure 6:
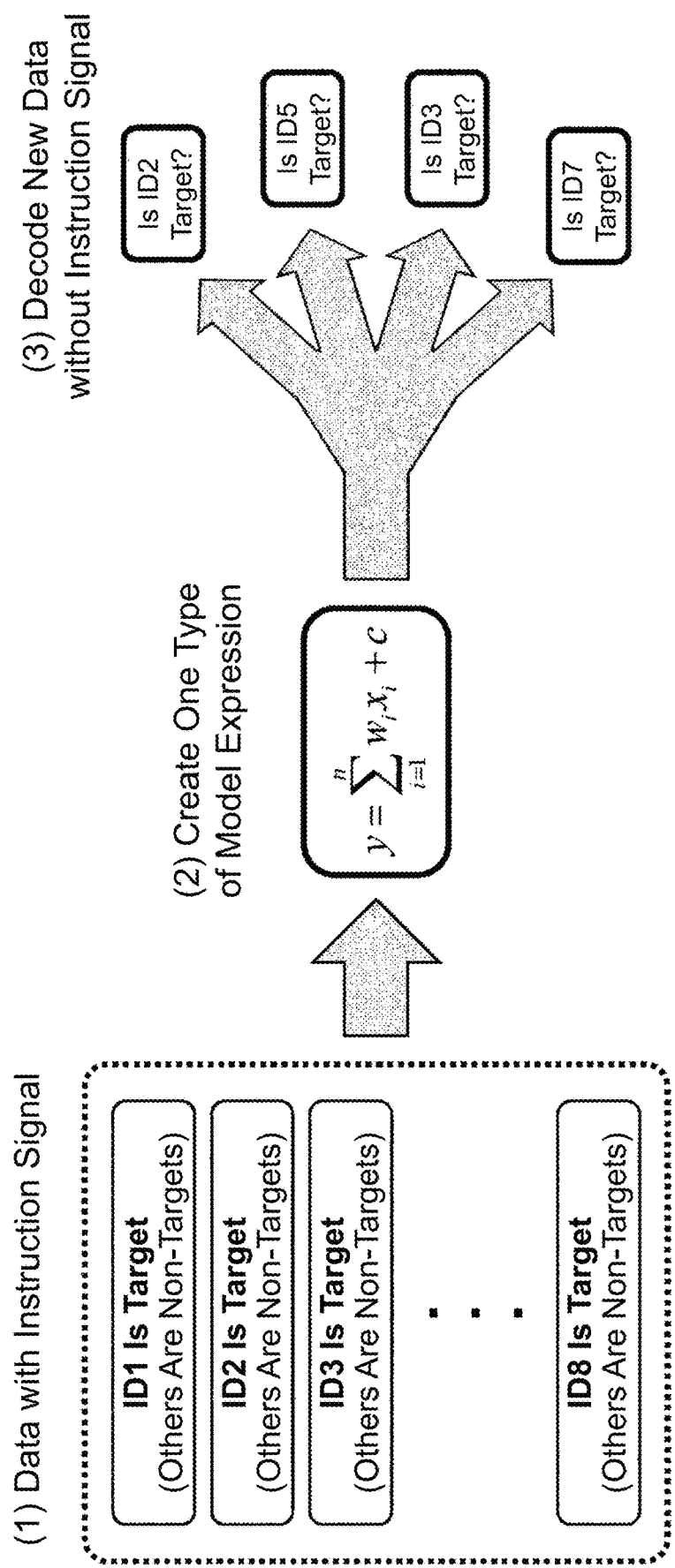
FIG. 6 is an explanatory drawing of a conventional brain wave decoding procedure that requires the instruction signal.

FIG. 5 is a drawing illustrating a comparison of the discrimination scores with respect to the target stimuli, when the respective stimuli are assumed as the target. When an analysis similar to those of ID2 and ID5 illustrated in FIG. 4 is performed on all the stimuli, and the discrimination scores with respect to the stimuli assumed as the target are compared with one another, the discrimination score ("accumulated discrimination score" of the vertical axis in the drawing) becomes maximum as was expected when ID2 is assumed as the target. Actually, this brain wave data has been set by the user assuming ID-2 as the target. It has been proven that the decoding has succeeded.

In the first embodiment, the expression of the discrimination score y has been described in the example where, as to the type of x, there are as many types (n) as the product of the number of channels (which corresponds to the number of measurement locations because the brain wave data are obtained at a plurality of measurement locations on the scalp of the head of the test subject) and data points (respective time windows after the respective stimuli). While the decoding method that does not require the instruction signal can instantly obtain the decoding result in units of one game (a plurality of blocks), when the number of the items in the discriminant model expression remains the same as in the conventional method, the number of data required for the optimization is possibly not sufficiently obtained. In such a case, the number of the items in the model expression, that is, the number of types of the weighting coefficient is substantially reduced by performing the dimensional compression, for example, by obtaining a channel average or using first and second principal components of the principal component analysis. For example, when eight types of stimuli (one type of target and seven types of non-targets) are presented during ten blocks, the stimulus presentation is performed 80 times. Thus, data series of 80 sets exists. Meanwhile, when components of data for each one set are voltage values for eight channels by 15 time points of one channel, that is, the total 120 pieces of voltage values, the number of data with respect to the number of the items in the model is only a ratio of less than one time. This makes the creation of the model impossible. Therefore, the use of the channel average can reduce the number of the items to eighth (15 pieces) and makes the ratio 5.3. This makes the creation of the model possible.

The examples described with reference to the embodiments and the like are intended to aid the reader in understanding the invention, which is not limited to the embodiments.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An intention decoding apparatus that analyzes brain waves to decode an intention of a person with motor impairment, the intention decoding apparatus comprising:
   a display on a sub-monitor for presenting to the person with motor impairment a plurality of stimulus events without an instruction signal, wherein a selected one of the plurality of stimulus events is a target stimulus event of the person with motor impairment and other stimulus events are non-target stimulus events; and
   a computer for measuring and collecting brain wave data of the person with motor impairment at a plurality of scalp locations on a head of the person with motor impairment during the presenting of the plurality of stimulus events to produce an electroencephalograph;
   wherein the computer is configured to perform a process to examine a dispersion by classifying the brain wave data of event-related potentials corresponding to the plurality of stimulus events into the one target stimulus event and the other non-target stimulus events among the plurality of stimulus events, wherein examining the dispersion is free from a prior calibration step, and wherein the brain wave data for the target stimulus event is different from the brain wave data for the other non-target stimulus event, and identifying a classification where the dispersion becomes maximum to identify the one target stimulus event in the classification as an intention of the person with motor impairment.

2. The intention decoding apparatus according to claim 1, wherein the process generates a plurality of discriminant model expressions without the instruction signal for each of the plurality of stimulus events of a discriminant function that discriminates the target stimulus event and the other non-target stimulus events among the plurality of stimulus events to calculate a discrimination score of the one target stimulus event, and
   identifies the classification of the one target stimulus event where the dispersion becomes maximum based on values of the obtained discrimination scores.

3. The intention conveyance assist apparatus of claim 1 further comprising
   a presentation unit that presents a decoding result of the intention decoding apparatus.

4. An intention conveyance assist system for a person with motor impairment comprising:
   a display on a sub-monitor for presenting to the person with motor impairment a plurality of stimulus events, wherein a selected one of the plurality of stimulus events is a target stimulus event of the person with motor impairment and other stimulus events are non-target stimulus events;
   a computer for measuring and collecting brain wave data of the person with motor impairment at a plurality of scalp locations on a head of the person with motor impairment during the presenting of the plurality of stimulus events to produce an electroencephalograph;
   wherein the computer processes the brain wave data from the electroencephalograph without prior calibration; and
   a presentation apparatus of a process result,
   wherein the display presents each of a plurality of stimulus events one or more times,
   wherein the electroencephalograph measures a brain wave immediately after the presentation of each one of the plurality of stimulus events by the display,
   wherein the computer performs a process without calibration to examine a dispersion by classifying brain wave data of event-related potentials corresponding to the plurality of stimulus events into the one target stimulus event and the other non-target stimulus events among the plurality of stimulus events, on all the stimulus events, and identifies a classification where the dispersion becomes a maximum to identify the one stimulus event in the classification as the intention of the person with motor impairment corresponding to the one target stimulus event, and
   wherein the presentation apparatus presents the process result.

5. An intention decoding method of analyzing brain waves to decode an intention of a person with motor impairment, the intention decoding method comprises generating a plurality of discriminant model expressions using brain wave data from a plurality of stimulus events provided to the person with motor impairment without an instruction signal, wherein each of the discriminant model expressions are of a discriminant function that discriminates one target stimulus event from other non-target stimulus events among the plurality of stimulus events to calculate a discrimination score for each of the one target stimulus events;
   examining a dispersion by classifying the brain wave data of event-related potentials corresponding to the plurality of stimulus eventsincluding the one target stimulus event and the other non-target stimulus events, and
   identifying a classification where the dispersion becomes maximum to identify the one target stimulus event in the classification as the intention of the person with motor impairment.

* * * * *